United States Patent
Berlinger et al.

(10) Patent No.: US 10,543,381 B2
(45) Date of Patent: *Jan. 28, 2020

(54) SYSTEM FOR MONITORING THE POSITION OF A PATIENT RECEIVING 4PI RADIATION THERAPY

(71) Applicant: Brainlab AG, Munich (DE)

(72) Inventors: Kajetan Berlinger, Munich (DE); Stephan Fröhlich, Aschheim (DE)

(73) Assignee: Brainlab AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/438,975

(22) Filed: Jun. 12, 2019

(65) Prior Publication Data

US 2019/0290934 A1  Sep. 26, 2019

Related U.S. Application Data

(62) Division of application No. 15/543,068, filed as application No. PCT/EP2016/068196 on Jul. 29, 2016, now Pat. No. 10,384,082.

(51) Int. Cl.
  *A61N 5/10* (2006.01)
(52) U.S. Cl.
  CPC ............ *A61N 5/1049* (2013.01); *A61N 5/107* (2013.01); *A61N 5/1031* (2013.01); *A61N 5/1045* (2013.01); *A61N 5/1067* (2013.01); *A61N 5/1071* (2013.01); *A61N 5/1075* (2013.01); *A61N 5/1077* (2013.01); *A61N 5/1081* (2013.01); *A61N 2005/1058* (2013.01);
(Continued)

(58) Field of Classification Search
  USPC ........................................................ 382/128
  See application file for complete search history.

(56) References Cited

U.S. PATENT DOCUMENTS

| 5,207,223 A | 5/1993 | Adler |
| 6,865,253 B2 | 3/2005 | Blumhofer et al. |

(Continued)

FOREIGN PATENT DOCUMENTS

| WO | 2011/0116830 A1 | 9/2011 |
| WO | 2012/019162 A1 | 2/2012 |

(Continued)

OTHER PUBLICATIONS

International Search Report and Written Opinion from corresponding International Application No. PCT/EP2016/068196 dated May 8, 2017. pp. 1-16.

(Continued)

*Primary Examiner* — Ishrat I Sherali
(74) *Attorney, Agent, or Firm* — Tucker Ellis LLP

(57) ABSTRACT

Disclosed is a method for determining a deviation of the position of an anatomical body part relative to a predetermined position defined by a radiation treatment plan. A monitoring image is taken of the anatomical body part at the instant that a predetermined control point defined in the treatment plan has been reached. The monitoring image is compared to a simulated image simulated from a planning image of the anatomical body from the perspective of a monitoring camera used to generate the monitoring image. The comparison allows for a determination of whether there is a positional deviation.

19 Claims, 7 Drawing Sheets

(52) U.S. Cl.
CPC ............... *A61N 2005/1059* (2013.01); *A61N 2005/1062* (2013.01); *A61N 2005/1074* (2013.01)

(56) References Cited

U.S. PATENT DOCUMENTS

| | | | |
|---|---|---|---|
| 7,906,770 B2 | 3/2011 | Otto | |
| 8,391,955 B2 | 3/2013 | Erbel et al. | |
| 8,873,710 B2 | 10/2014 | Ling et al. | |
| 9,489,734 B2* | 11/2016 | Gum | A61N 5/1049 |
| 9,508,145 B2* | 11/2016 | Gum | A61N 5/1049 |
| 9,730,654 B2 | 8/2017 | Erbel et al. | |
| 10,092,251 B2 | 10/2018 | Virshup et al. | |
| 10,384,082 B2* | 8/2019 | Berlinger | A61N 5/1045 |
| 2008/0298550 A1 | 12/2008 | Otto | |
| 2013/0142310 A1 | 6/2013 | Fahimian et al. | |
| 2013/0287167 A1 | 10/2013 | Gum et al. | |
| 2018/0200536 A1 | 7/2018 | Fontanarosa et al. | |

FOREIGN PATENT DOCUMENTS

| | | |
|---|---|---|
| WO | 2014/0144469 A1 | 9/2014 |
| WO | 2015/0120906 A1 | 8/2015 |

OTHER PUBLICATIONS

Mostafavi H., et al., "Detection and Localization of Radiotherapy Targets by Template Matching", Engineering in Medicine and Biology Society, (2012), 35th Annual International Conference of the IEEE EMBS, pp. 6023-6027.

* cited by examiner

Figure 1: Conventional Plan with static beams

Figure 2: 4Pi – Non Isocentric Plan with static beams

Figure 3: Same plan as in Figure 2 but now with updated MLC

Figure 4: Conventional Rapid-Arc

Figure 5: 4 Pi Rapid-Arc

SYSTEM FOR MONITORING THE POSITION OF A PATIENT RECEIVING 4PI RADIATION THERAPY

RELATED APPLICATION DATA

This application is a Divisional of application Ser. No. 15/543,068, filed on Jul. 12, 2017, which is a national phase application of International Application No. PCT/EP2016/068196 filed Jul. 29, 2016, and published in the English language.

The present invention relates to a computer-implemented method for determining a deviation between a planned and an actual relative position between an anatomical body part of a patient's body, a corresponding computer program, a non-transitory program storage medium storing such a program and a computer for executing the program, as well as a system for determining a deviation between a planned and an actual relative position between an anatomical body part of a patient's body, the system comprising an electronic data storage device and the aforementioned computer.

TECHNICAL BACKGROUND

4π radiation therapy is a new treatment strategy for increasing dose conformity and normal tissue sparing using e.g. highly non-coplanar treatment angles and non-isocentric treatment angles. 4π radiation therapy even includes applying the thereby resulting changes in treatment couch position (translational and rotational) during beam-on, e.g. during an arc treatment. Image-guided radiotherapy (IGRT) systems like ExacTrac® (a product of Brainlab AG) are so far only prepared to monitor the position of a target having a fixed geometric alignment to the treatment machine (alignment of treatment couch to the linear accelerator (Linac) during beam-on. So far any movement of the couch during beam-on has been suppressed.

IGRT systems like ExacTrac® are so far only prepared to monitor the position of a target having a fixed geometric alignment to the treatment machine (alignment of treatment couch to Linac) during beam-on. So far, there has been one planned alignment of patient to treatment system during beam-on in radiotherapy (before 4π radiation therapy was introduced).

The present invention is designed to provide an IGRT system that is capable of monitoring the position of the patient even if the alignment between couch/treatment table and the linear accelerator changes during beam-on.

The present invention can be used in connection with a system for image-guided radiotherapy such as ExacTrac®, a product of Brainlab AG.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses determining a deviation of the position of an anatomical body part relative to a predetermined position defined by a radiation treatment plan. To this end, a monitoring image is taken of the anatomical body part at the instant that a predetermined control point defined in the treatment plan has been reached. The monitoring image is compared to a simulated image simulated from a planning image of the anatomical body from the perspective of a monitoring camera used to generate the monitoring image. The comparison allows to determine whether there is a positional deviation or not.

General Description of the Present Invention

In this section, a description of the general features of the present invention is given for example by referring to possible embodiments of the invention.

In general, the invention reaches the aforementioned object by providing, in a first aspect, a computer-implemented medical data processing method for determining a deviation between a planned and an actual relative position between an anatomical body part of a patient's body. The method comprises executing, on at least one processor of at least one computer (for example at least one computer being part of the navigation system), the following exemplary steps which are executed by the at least one processor.

In a (for example first) exemplary step, planned control point data is acquired which describes (for example, defines or represents) predetermined (for example, planned, more specifically at least one of known or fixed) control points each describing a predetermined operational state (in general, at least one predetermined operational state, including a plurality of operational states, wherein in one example all operational states are different from one another) of the radiation treatment apparatus, the control points (specifically, the operational states) having a predetermined (for example fixed) temporal order in which they are planned to be assumed by the radiation treatment apparatus and each control point being associated with a predetermined planned relative position between the anatomical body part and a monitoring imaging apparatus (which can be part of the radiation treatment apparatus). Within this disclosure, radiation treatment comprises at least radiotherapy or radiosurgery.

In one example of this (first) exemplary step, the radiation treatment apparatus assumes the, for example all of the, predetermined control points while a treatment beam source included in the radiation treatment apparatus is activated. The treatment beam source can be a source of ionizing radiation such as a linear accelerator or an x-ray tube. The treatment beam source being activated corresponds to a "beam-on" status of the radiation treatment apparatus. This means that the treatment beam source such as a linear accelerator is energized (for example, that the accelerator voltage is applied) but that the treatment beam need not necessarily be emitted from the radiation treatment apparatus, for example it may not be emitted from the radiation treatment apparatus despite the treatment beam source being energized if the shutter (and/or the collimator such as a multi-leaf collimator (MLC)) is closed (under such circumstances, the anatomical body part is not irradiated with treatment radiation.

In one example, the control points are associated with positions (for example at least one of the predetermined relative positions between the anatomical body part and the monitoring imaging apparatus or the below-described planned relative position between the anatomical body part and the radiation treatment apparatus) lying on a trajectory of the treatment beam source which it takes while being activated.

For example, the disclosed method comprises the following steps:

planned position data is acquired which describes (for example, defines or represents) a (predetermined, for example known but not necessarily fixed) planned relative position between the anatomical body part and the radiation treatment apparatus for each one of the control points (that planned relative position may be defined by a treatment position, i.e. the position of the anatomical body part, and the angle of a patient support unit of the radiation treatment apparatus such as a treatment table);

monitoring imaging apparatus calibration data is acquired which describes (for example, defines or represents) a (predetermined, for example known) relative position between the radiation treatment apparatus and the monitoring imaging apparatus; and the planned relative position between the anatomical body part and the monitoring imaging apparatus is determined based on the planned position data and the monitoring imaging apparatus calibration data (for example, by adding the planned relative position between the anatomical body part and the radiation treatment apparatus to the relative position between the radiation treatment apparatus and the monitoring imaging apparatus—the output will then be the planned relative position between the anatomical body part and the monitoring imaging apparatus).

In a general example of the disclosed method, the anatomical body part is not positioned in an isocentre of the radiation treatment apparatus so that the relative position between the anatomical body part and the radiation treatment apparatus need not necessarily define the isocentre position. However, the anatomical body part may alternatively be positioned in the isocentre of the radiation treatment apparatus.

In a further (for example second) exemplary step, current control point data is determined which describes (for example, defines or represents) whether the radiation treatment apparatus has assumed a predetermined control point. The current control point data is determined for example by gathering at least one of analogue or digital signals from different operational units of the radiation treatment apparatus which represent a variable characterising the current operational status of the respective operational unit. The different operational units may be at least one of a treatment beam source, a patient support unit (e.g. a treatment table), a shutter, or a collimator (e.g. a multi-leaf collimator). This procedure can be embodied by the following steps, which are an example of this (second) exemplary step:

acquiring, at the at least one processor, current operational state data describing a current operational state of the radiation treatment apparatus;

wherein the current control point data is determined based on the current operational state data and the planned control point data.

In one example, the current control point data is determined by comparing the current operational state to the predetermined operational states. The current control point data describes that the radiation treatment apparatus has assumed a predetermined control point if the comparison results in that the current operational state corresponds (for example, is equal or at least substantially equal) a predetermined operational state. For example, a control point is said to have been reached (assumed) if the current operational state is equal or at least substantially equal to the predetermined operational state.

In a further (for example third) exemplary step, monitoring image data is acquired which describes (for example, defines or represents) at least one digital medical monitoring image of the anatomical body part in at least one monitoring relative position between the anatomical body part and the monitoring imaging apparatus (i.e. the monitoring has been generated in a perspective from the monitoring imaging apparatus onto the anatomical body part). The monitoring imaging apparatus is used to generate the monitoring image. The monitoring can be an x-ray camera (such as a stereo x-ray camera), a thermal camera (for detection of infrared light emitted by the anatomical body part), a camera suitable for detection of structured light (for example in the visual wavelength range, for the detection of corresponding light reflections from the surface of the anatomical body part), a digital still image camera, a digital moving image (video) camera, or a sonography device. Consequently, the monitoring image data is describable in two or three dimensions (depending also on the used monitoring imaging apparatus). The method according to any one of the preceding claims, wherein the monitoring image data is or has been generated by x-ray imaging, thermal imaging, structured light imaging, digital still imaging, digital video imaging, or sonography.

In one example of this (third) exemplary step, the monitoring image data is acquired on the current control point data. For example, the monitoring image data is generated if the current control point data describes that the radiation treatment apparatus has assumed a predetermined control point (i.e. when the radiation treatment apparatus has assumed/reached the predetermined control point).

In a further (for example fourth) exemplary step, patient image data is acquired which describes (for example, defines or represents) a predetermined medical image of the anatomical body part. The predetermined medical image will generally be a planning image for planning radiation treatment of the anatomical body part. For example, the patient image data is describable in three dimensions (i.e. is three-dimensional image data such as tomographic image data, e.g. a computed x-ray tomography, a magnetic resonance tomography, or a sonography). The patient image data in one example has been generated before the disclosed method is executed is then used as an input to the disclosed method.

In a further (for example fifth) exemplary step, comparison image data is determined which describes (for example, defines or represents) at least one digital medical comparison image of the anatomical body part in the monitoring relative position. The comparison image data is determined based on the patient image data and the current control point data and the planned control point data. The comparison image is generated in a perspective from the monitoring imaging apparatus to the representation of the anatomical body part in the patient image data. That perspective may be defined in a reference system defining positions in the patient image data. To that effect, for example positional transformation data describing (for example defining or representing) a positional transformation between a reference system used for defining positional information in the monitoring image data and a reference system used for defining positional information in the patient image data can be acquired, wherein the positional deviation data is determined based on the positional transformation data. In the framework of this disclosure, a transformation is understood to be a linear mapping embodied by a matrix. In one example, the positional transformation data is acquired based on the monitoring imaging apparatus calibration data, for example the positional transformation is predetermined (for example at least one of known or fixed), and the positional transformation data is included in e.g. the monitoring imaging apparatus calibration data or another predetermined dataset. The positional transformation between a reference system used for defining positional information in the monitoring image data and a reference system used for defining positional information in the patient image data can then be understood to be a basis transformation between the two reference systems. The comparison image data can thus be determined by applying the positional transformation to the planned relative position or the monitoring relative position, for example so that both positions are defined in a common coordinate system.

In one example, the comparison image data is generated substantially at the point in time at which, for example while, the radiation treatment apparatus assumes the predetermined control point. For example, the comparison image data is generated if the current control point data describes that the radiation treatment apparatus has assumed a predetermined control point (i.e. when the radiation treatment apparatus has assumed/reached the predetermined control point).

The comparison image is generated from the patient image data and is describable in for example two dimensions, for example is a digitally reconstructed radiograph (DRR), or three dimensions, for example is a surface reconstruction from a thermal image or a structured light image.

In a further (for example sixth) exemplary step, position deviation data is determined which describes (for example, defines or represents) a positional deviation between the planned relative position associated with the planned control point assumed by the radiation treatment apparatus on the one hand and the monitoring relative position on the other hand. The position deviation data is determined based on the comparison image data and the monitoring image data. Specifically, the positional deviation is determined by comparing the comparison image to the monitoring image, i.e. the comparison image is used as a comparison for the monitoring image. For example, the positional deviation has been or is determined by applying an image fusion algorithm, for example a rigid image fusion algorithm, to the monitoring image data and the patient image data. The positional deviation will be the output of that image fusion operation.

In one specific example of the disclosed method, the planned control point data comprises planned position data describing planned relative positions between the anatomical body part and the treatment beam source and, for each at least one planned relative position, the operational state as a reference dose being a predetermined amount of a planned treatment dose associated with the respective at least one planned relative position, wherein each control point is described by at least one of planned relative positions. Then, the current control point data comprises monitoring dose data describing the current operational state as a monitoring dose being an amount of the planned treatment dose associated with at least one of the monitoring image or the at least one actual relative position between the anatomical body part and the treatment beam source. The method can then comprise a step of determining, based on the monitoring dose data and the planned control point data, corresponding reference dose data describing (for example, defining or representing) a corresponding reference dose being the reference dose corresponding best within a predetermined interval to the monitoring dose. The comparison image data is then determined based on the patient image data and the corresponding reference dose data, wherein the monitoring relative position is the planned relative position between the anatomical body part and the monitoring imaging apparatus. The corresponding reference dose is the reference dose closest at least within a predetermined interval to the monitoring dose.

Alternatively or additionally, the planned operational states may within the framework of the disclosed method be respectively (and, in a further example, each) defined by at least one of a patient support unit angle (e.g. a treatment table angle), a patient support unit position (e.g. a treatment table position), a target position, a treatment beam source angle (a gantry angle), a collimator geometry, at least one treatment beam source movement speed value (a gantry movement speed value), or at least one applied dose rate value (describing a value of an applied dose).

In an example of the disclosed method, the at least one planned relative position, the at least one monitoring relative position are described by vectors and the positional deviation is described by a matrix, for example a 4×4 matrix. The term "position" in the framework of this disclosure does not necessarily imply a single point in space defining a position but is rather understood to denote a spatial quantity defined by its absolute value and direction.

The disclosed method in one example comprises the following further steps:
  acquiring deviation threshold data describing a threshold for the positional deviation; and
  determining, based on the position deviation data and the deviation threshold data, treatment apparatus control data describing a command to be issued, by the at least one processor, to the radiation treatment apparatus.

For example, the treatment apparatus control data (specifically, the command) is determined by comparing the positional deviation to the threshold for the positional deviation, and wherein the command describes for example at least one of deactivation of a treatment beam source of the radiation treatment apparatus, interruption of a treatment beam emitted by the treatment beam source, or relative movement of the anatomical body part relative to the treatment beam source.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a fifth aspect, the invention is directed to a system for determining a deviation between a planned and an actual relative position between an anatomical body part and a treatment beam source, the system comprising:
  a) the at least one computer according to the preceding claim;
  b) at least one electronic data storage device storing at least the planned control point data; and
  c) a medical imaging device for generating the monitoring image, the medical imaging device being operably coupled to the at least one computer for transmitting a signal to the at least one computer corresponding to the monitoring image data; and d) the radiation treatment apparatus comprising a treatment beam source, wherein the at least one computer is operably coupled to the at least one electronic data storage device for acquiring, from the at least one data storage device, at least one of patient image data or the planned control point data, and for issuing a command to the radiation treatment apparatus for controlling the treatment beam source on the basis of the position deviation data.

In an example of the fifth aspect, the system (specifically, the radiation treatment apparatus) further comprises a patient support unit such as a treatment table on which a patient and/or the anatomical body part can be placed. The patient support unit may be driven so that its position for example relative the (remainder of) the radiation treatment apparatus Then, the at least one computer may also be operably coupled to the patient support unit for controlling its position (by driving it) on the basis of the position deviation data.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of radiotherapy or radiosurgery. More particularly, the invention does not involve or in particular comprise or encompass any surgical or therapeutic activity. The invention is instead directed as applicable to positioning a patient relative to the treatment device for example before any radiotherapy or radiosurgery ensues. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, ,a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The present invention relates to the field of controlling a treatment beam. The treatment beam treats body parts which are to be treated and which are referred to in the following as "treatment body parts". These body parts are for example parts of a patient's body, i.e. anatomical body parts.

Ionising radiation is an example of radiation emittable by the radiation treatment apparatus and is used for example for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of an anatomical body part.

DESCRIPTION OF THE FIGURES

In the following, the invention is described with reference to the appended figures which give background explanations and represent specific embodiments of the invention. The scope of the invention is however not limited to the specific features disclosed in the context of the figures, wherein.

FIGS. 1 to 3 give an impression of what 4 π radiotherapy means, in this case for a conventional treatment plan with static beams. This plan shall improve Dose Conformity (Treated Volume/Planned Target Volume) by moving patient closer to treatment source for every beam, and thereby enabling an improved beam shaping (adapt MLC leafs to target contour). The isocentres (positions of the treatment target) are changed between the beams/between the beam-on intervals.

FIGS. 4 and 5 illustrate what 4 π radiotherapy means for arc treatments. FIG. 4 shows a conventional rapid arc treatment. Whenever one of parameters gantry speed, dose rate or shape is changed a new control point is introduced. However, the geometrical alignment between the treatment table and the radiation treatment apparatus is not changed during beam-on. In contras thereto, according to FIG. 5, a new control point is defined whenever the isocentre position (in this case, the relative position between the anatomical body part and the radiation treatment apparatus) changes, and thus the relative position between the treatment table the radiation treatment apparatus changes. The expression "control point" does not necessarily define a point in space but a milestone (the begin of another segment of a treatment plan) in the process of emitting a treatment beam along an arc-shaped trajectory.

FIG. 5 shows a 4π-non-isocentric arc radiotherapy treatment: besides shape of a collimator (multi-leaf collimator), gantry speed and dose rate, the isocentre position changes, and yields new control points. The table angle can additionally be modified at every control point.

FIG. 6 is a flow diagram illustrating the basic steps of the disclosed method in accordance with the first aspect, which in the illustrative example of FIG. 6 starts with a step S11 of acquiring the planned control point data. In subsequent step S12, the current control point data is determined, followed by step S13 which encompasses acquiring the monitoring image data. Then, step S14 acquires the patient image data. Subsequent step S15 is directed to determining the comparison image data. Steps S11 to S15 serve as input steps for the last step shown in FIG. 6 which is step S16 encompassing determination of the position deviation data.

FIG. 7 shows an embodiment of the disclosed method in accordance with the first aspect. The monitoring system (the monitoring imaging apparatus) knows in real-time any change in treatment isocentre (target) position and couch kick (movement increment). Once a new control point/a new milestone in current dose application has been reached, a new changed (corresponding to the above-described comparison image) is created. Thus, the just acquired live data can be compared to that reference image in order to get the positional difference data. The comparison itself would be in terms of the ExacTrac® radiation therapy apparatus a 2D/3D fusion using DRRs (digitally rendered radiographs representing the aforementioned comparison image data) created from a CT scan. But the comparison could also be any surface matching/point could registration method, in general any signal registration method that is known in the field.

Figure 1:
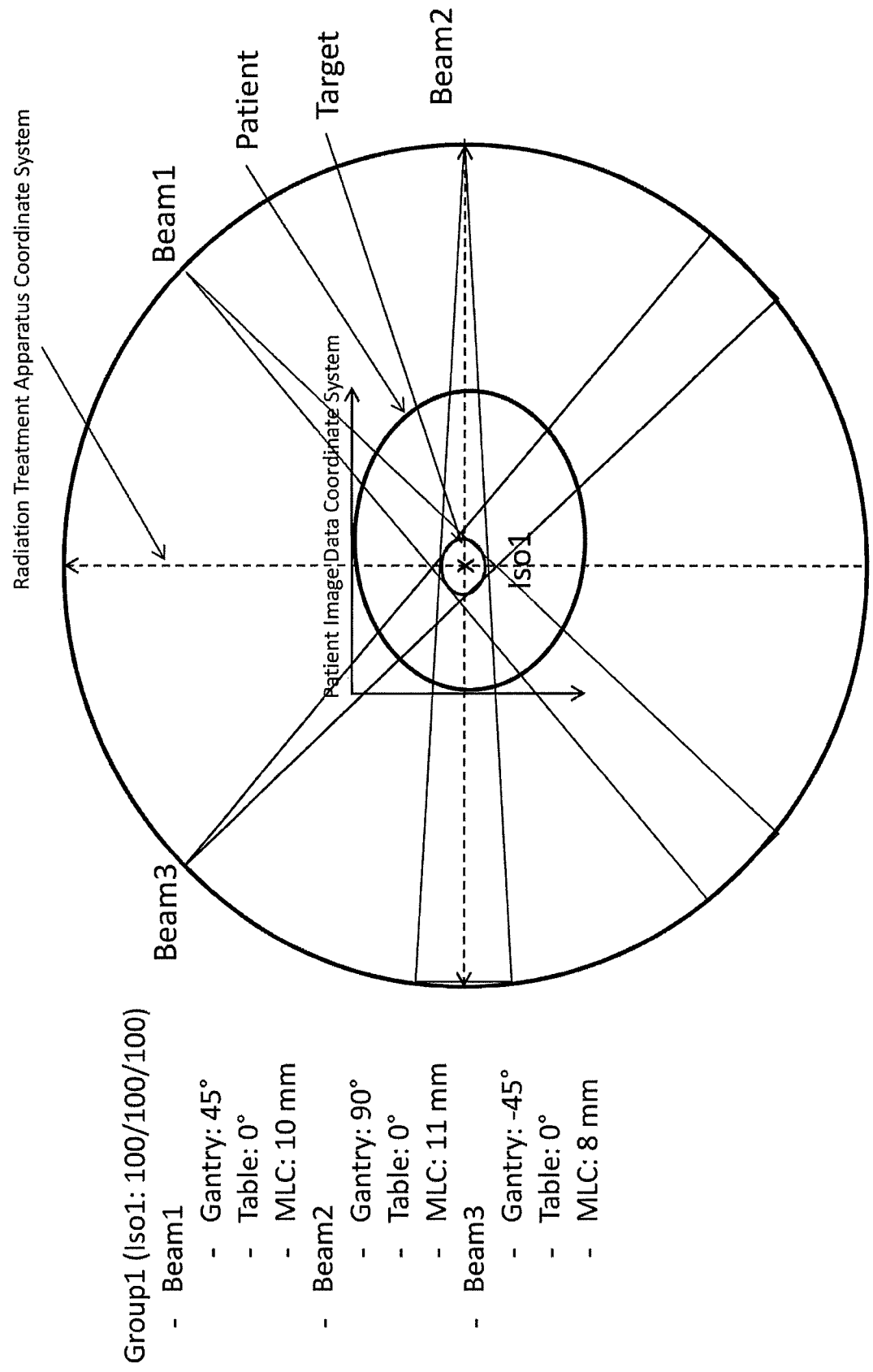
FIGS. 1 to 3 give an explanation of 4 π radiotherapy.
Figure 2:
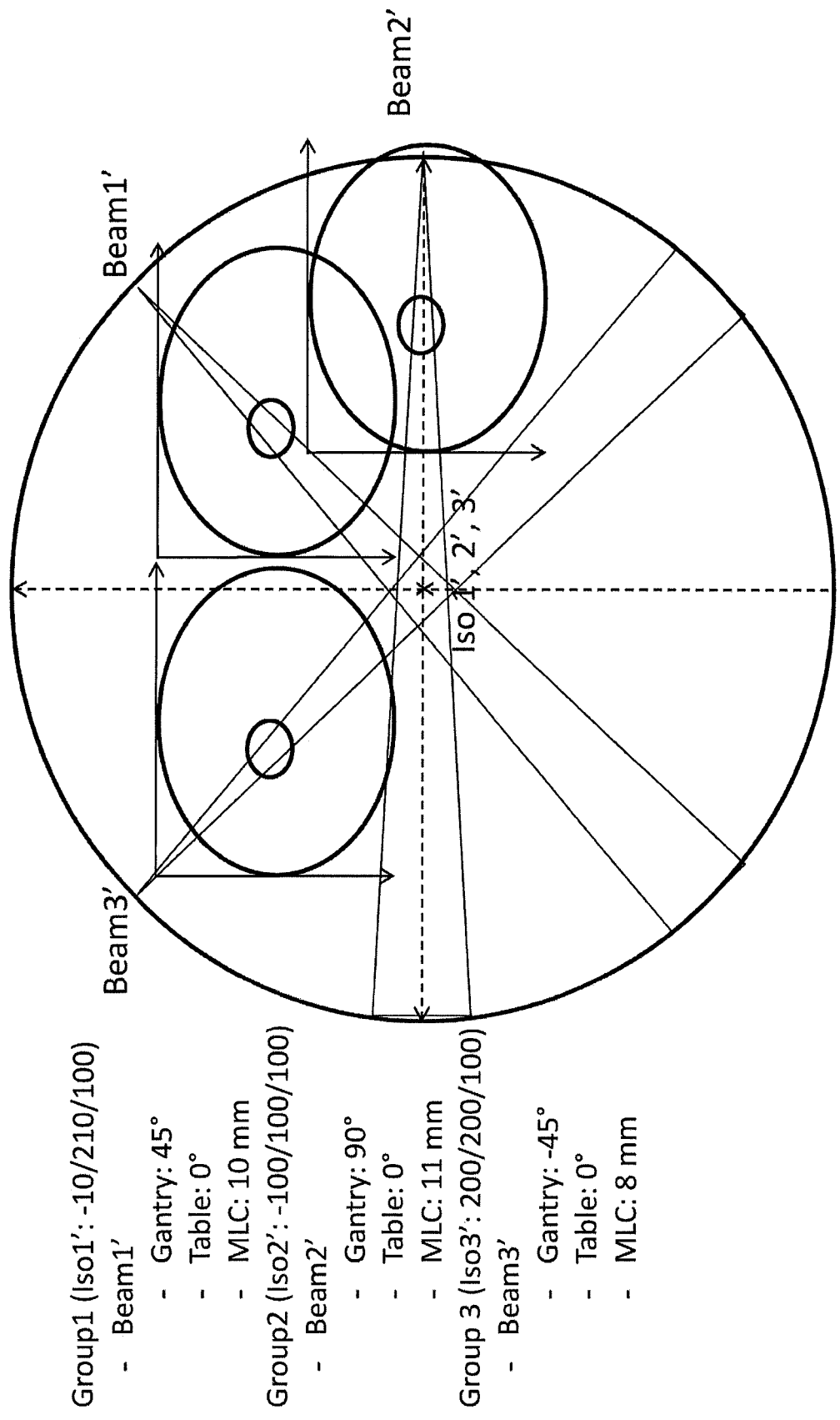
Figure 3:
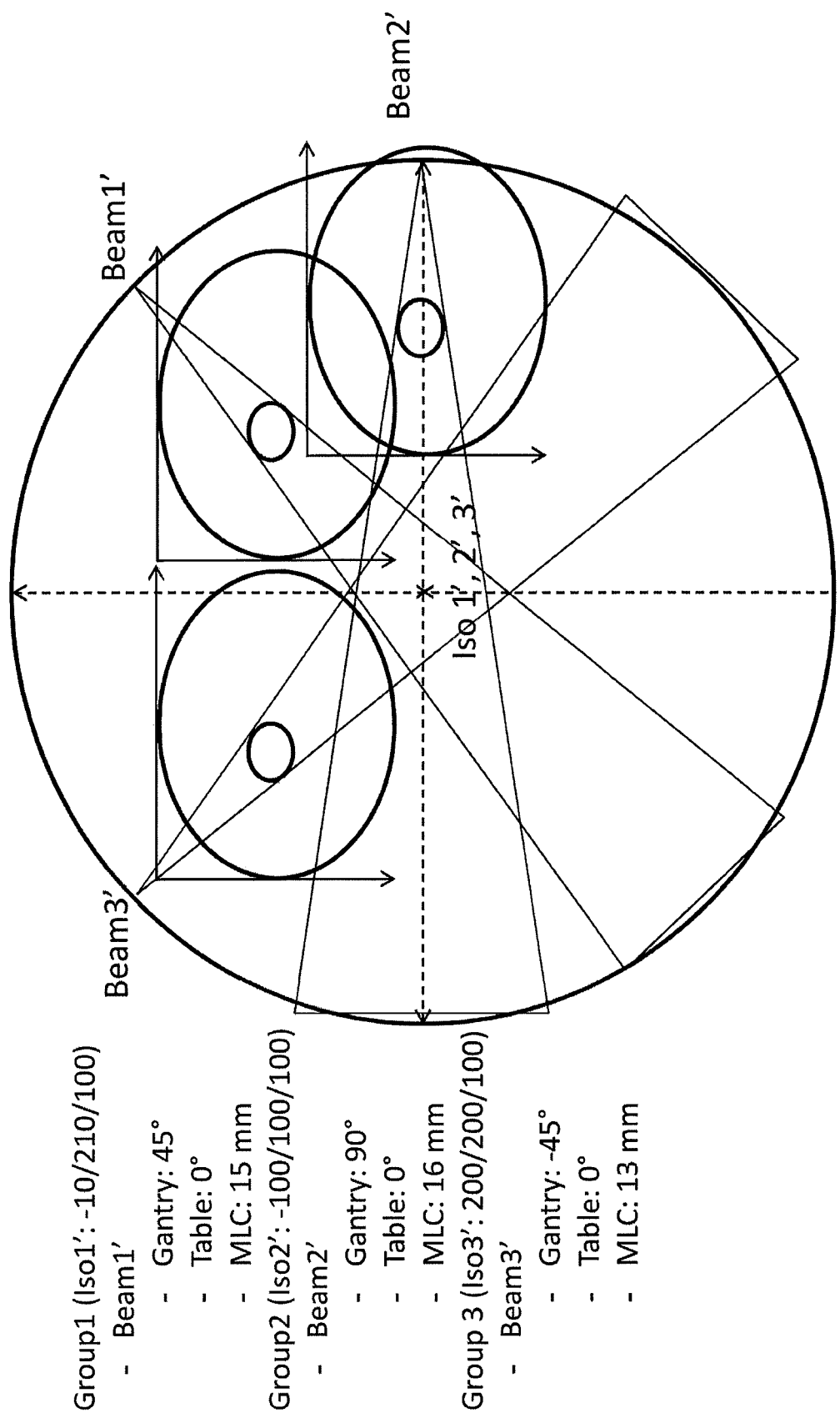
Figure 4:
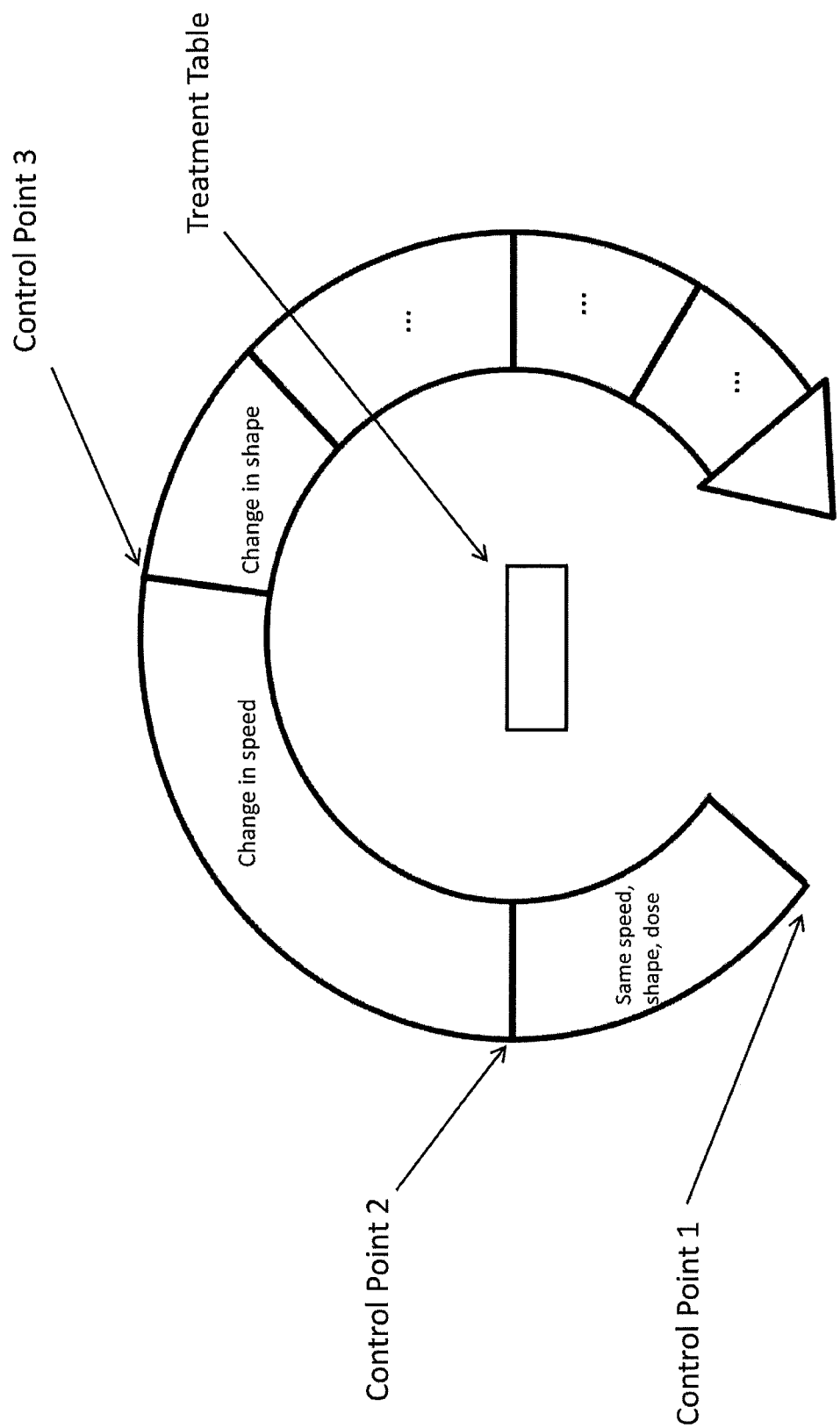
FIGS. 4 to 5 illustrate 4 π radiotherapy for an arc representing a trajectory for moving a treatment beam source.
Figure 5:
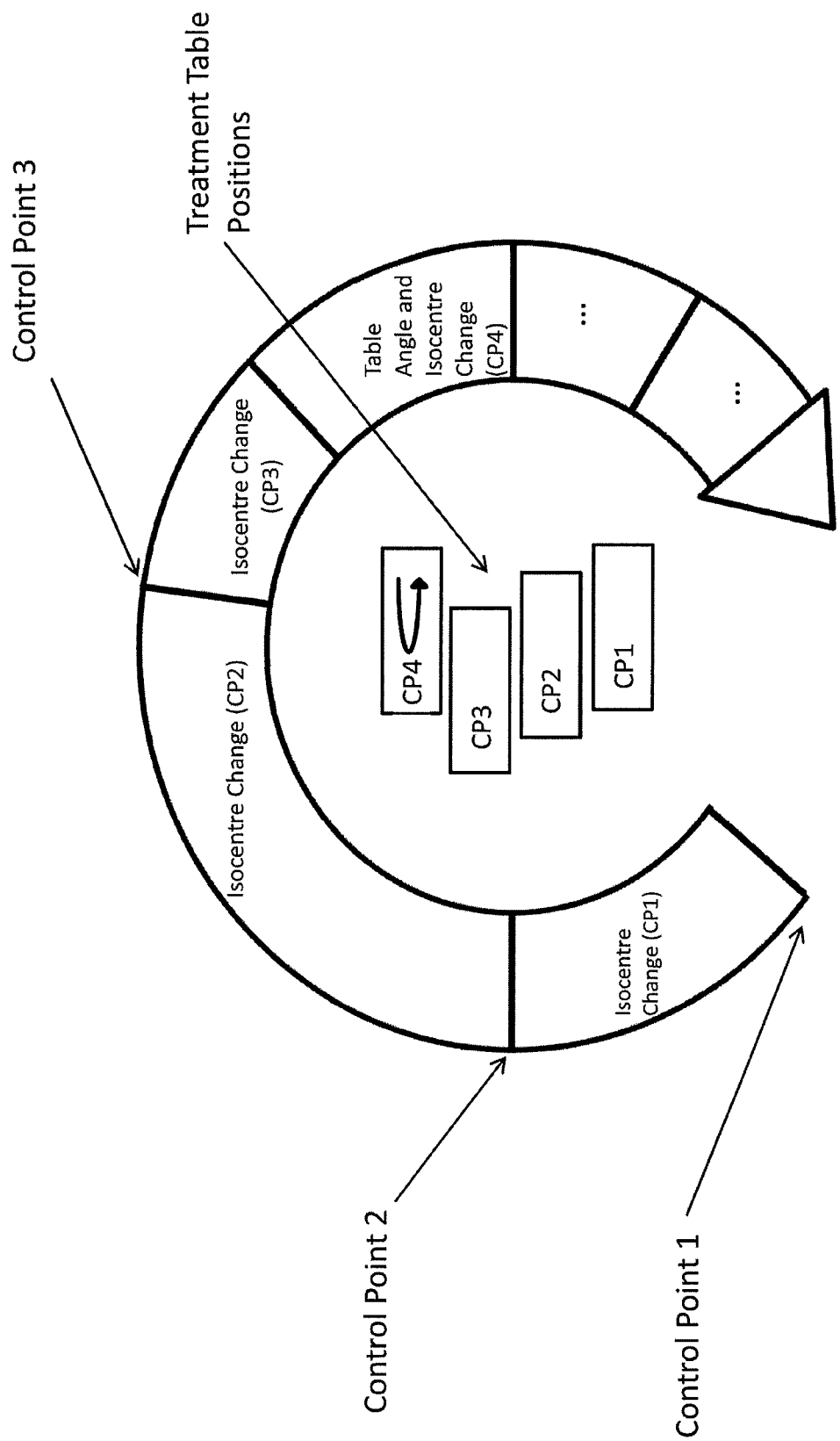
Figure 6:
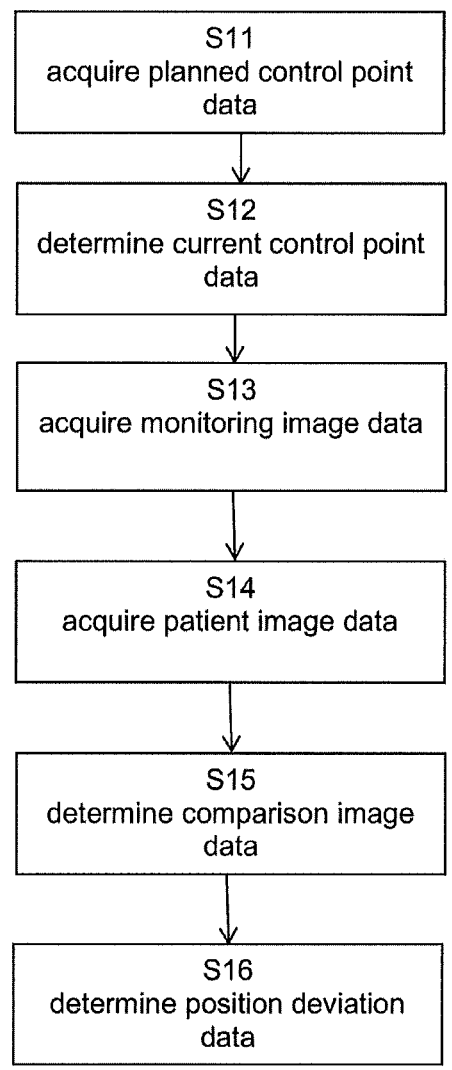
FIG. 6 is a flow diagram representing the basic steps of the disclosed method.
Figure 7:
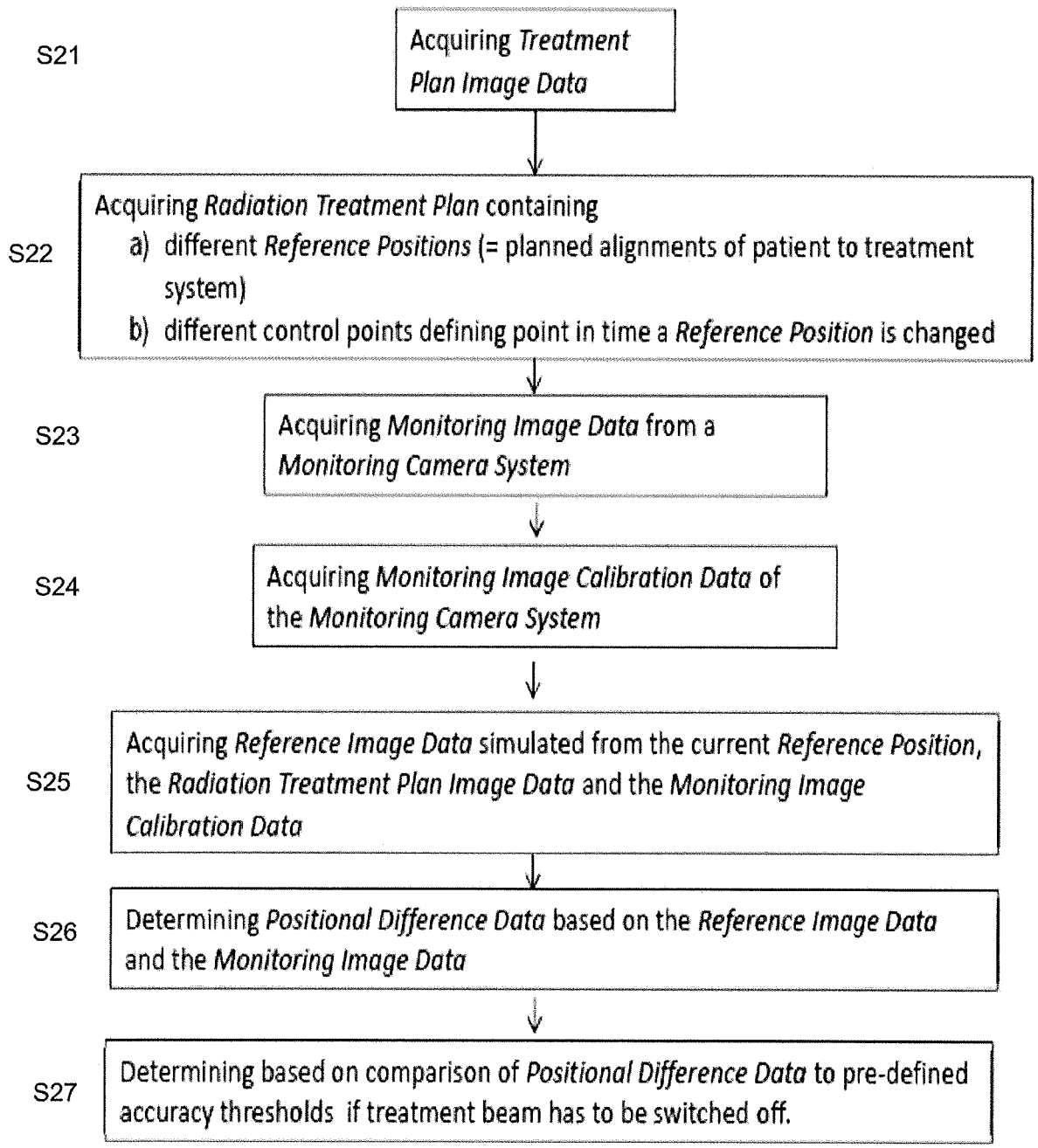
FIG. 7 is a flow diagram representing an embodiment of the disclosed method.

The comparison image data can be e.g. one of a digitally reconstructed radiograph (DRR), a simulated thermal image, a point cloud generated from a thermal image or a point cloud generated from a structured light image. The data used to create the comparison image is:

the camera calibration (corresponding to the aforementioned monitoring imaging apparatus calibration data); and the current isocentre (treatment target) position and couch angle (=currently desired/planned alignment of the patient to the radiation treatment system), The embodiment of the disclosed method shown in FIG. 7 can be outlined as follows:

(S21) acquiring radiation treatment plan image data describing a digital image of the patient (such as a planning CT);

(S22) acquiring a radiation treatment plan from a radiation treatment planning system, the radiation treatment plan defining at least one reference position (corresponding to the aforementioned planned relative position between the anatomical body part and the radiation treatment apparatus and/or the monitoring imaging apparatus) in the radiation treatment plan image data, the reference position defining the planned alignment of the patient to the radiation treatment system, and the radiation treatment plan defining changes in the reference position depending on the progress of emitting the treatment beam (and/or a predetermined amount of the planned treatment dose);

(S23) acquiring the monitoring image data from a monitoring camera system (representing the monitoring imaging apparatus), the monitoring image data describing a current digital image of the anatomical body part;

(S24) acquiring monitoring image calibration data defining the . geometric camera calibration of the monitoring camera system to the radiation treatment system (the monitoring image calibration data corresponding to the monitoring imaging apparatus calibration data);
(S25) acquiring the reference image data (corresponding to the above-described comparison image data) simulated from the current reference position and the radiation treatment plan image data and the monitoring image calibration data;
(S26) determining positional difference data (corresponding to the position deviation data) based on the reference image data and the monitoring image data;
(S27) determining the treatment apparatus control data.

It is claimed:

1. A method for determining a deviation between a planned and an actual relative position between an anatomical body part of a patient's body and a radiation treatment apparatus, the method comprising executing, on at least one processor, steps of:
   a) acquiring, at the at least one processor, planned control point data describing predetermined control points each describing a predetermined operational state of the radiation treatment apparatus, the control points having a predetermined temporal order in which they are planned to be assumed by the radiation treatment apparatus and each control point being associated with a predetermined planned relative position between the anatomical body part and a monitoring imaging apparatus, wherein
      the planned control point data comprises planned position data describing planned relative positions between the anatomical body part and a treatment beam source of the radiation treatment apparatus and, for each at least one planned relative position, the operational state as a reference dose being a predetermined amount of a planned treatment dose associated with the respective at least one planned relative position, wherein each control point is described by at least one of planned relative positions;
   b) determining, at the at least one processor, current control point data describing whether the radiation treatment apparatus has assumed a predetermined control point, wherein the current control point data comprises monitoring dose data describing the current operational state as a monitoring dose being an amount of the planned treatment dose associated with at least one of a monitoring image or the at least one actual relative position between the anatomical body park and the treatment beam source;
   c) acquiring, at the at least one processor, monitoring image data describing at least one digital medical monitoring image of the anatomical body part in at least one monitoring relative position between the anatomical body part and the monitoring imaging apparatus, wherein the monitoring imaging apparatus is used to generate the monitoring image;
   d) acquiring, at the at least one processor, patient image data describing a predetermined medical image of the anatomical body part;
   e) determining, by the at least one processor and based on the monitoring dose data and the planned control point data, corresponding reference dose data describing a corresponding reference dose being the reference dose corresponding best within a predetermined interval to the monitoring dose;
   f) determining, by the at least one processor and based on the patient image data and the corresponding reference dose data, comparison image data describing at least one digital medical comparison image of the anatomical body part in the monitoring relative position, wherein the monitoring relative position is the planned relative position between the anatomical body part and the monitoring imaging apparatus; and
   g) determining, by the at least one processor and based on the comparison image data and the monitoring image data, position deviation data describing a positional deviation between (i) the planned relative position associated with the planned control point assumed by the radiation treatment apparatus and (ii) the monitoring relative position on the other hand,
   the method further comprising at least one of the following steps h1) and h2):
      h1) generating the comparison image data if the current control point data describes that the radiation treatment apparatus has assumed a predetermined control point, or
      h2) generating the monitoring image data if the current control point data describes that the radiation treatment apparatus has assumed a predetermined control point.

2. The method according to claim 1, wherein the monitoring image data is acquired, at the at least one processor, based on the current control point data.

3. The method according to claim 1, wherein the comparison image data is generated substantially at the point in time at which the radiation treatment apparatus assumes the predetermined control point.

4. The method according to claim 1, wherein the monitoring image data is describable in two or three dimensions.

5. The method according to claim 1, wherein the patient image data is tomographic image data and the comparison image is generated from the patient image data and is describable in two dimensions, or three dimensions.

6. The method according to claim 1, wherein the monitoring image data is generated by at least one of x-ray imaging, thermal imaging, structured light imaging, digital still imaging, digital video imaging, or sonography.

7. The method according to claim 1, wherein determining the comparison image data comprises;
   acquiring, at the at least one processor, positional transformation data describing a positional transformation between a reference system used for defining positional information in the monitoring image data and a reference system used for defining positional information in the patient image data, wherein
   the positional deviation data is determined, by the at least one processor, based on the positional transformation data.

8. The method according to claim 7, wherein the comparison image data is determined, by the at least one processor, by applying the positional transformation to the planned relative position between the anatomical body part and the monitoring imaging apparatus or to the monitoring relative position.

9. The method according to claim 7, wherein the positional transformation is determined by applying an image fusion algorithm to the monitoring image data and the patient image data.

10. The method according to claim 1, comprising:
    acquiring, at the at least one processor, planned position data describing a planned relative position between the anatomical body part and the radiation treatment apparatus for each one of the control points;

acquiring, at the at least one processor, monitoring imaging apparatus calibration data describing a relative position between the radiation treatment apparatus and the monitoring imaging apparatus, wherein the planned relative position between the anatomical body part and the monitoring imaging apparatus is determined, by the at least one processor, based on the planned position data and the monitoring imaging apparatus calibration data.

11. The method according to claim 1, wherein the corresponding reference dose is the reference dose closest at least within a predetermined interval to the monitoring dose.

12. The method according to claim 1, wherein the planned operational states are respectively defined by at least one of a patient support unit angle, a patient support unit position, a target position, a treatment beam source angle, a collimator geometry, at least one treatment beam source movement speed value, or at least one applied dose rate value.

13. The method according to claim 1, wherein the anatomical body part is not positioned in an isocenter of the radiation treatment apparatus.

14. The method according to claim 1, wherein the radiation treatment apparatus assumes the predetermined control points while the treatment beam source of the radiation treatment apparatus is activated.

15. The method according to claim 1, wherein the at least one planned relative position, and the at least one monitoring relative position are described by vectors and the positional is described by a matrix.

16. The method according to claim 1, comprising:
acquiring deviation threshold data describing a threshold for the positional deviation;
determining, by the at least one processor and based on the position deviation data and the deviation threshold data, treatment apparatus control data describing a command to be issued, by the at least one processor, to the radiation treatment apparatus.

17. The method according to claim 16, wherein the treatment apparatus control data is determined by comparing the positional deviation to the threshold for the positional deviation, and wherein the command describes at least one of deactivation of the treatment beam source of the radiation treatment apparatus, interruption of a treatment beam emitted by the treatment beam source, or relative movement of the anatomical body part relative to the treatment beam source.

18. A non-transitory computer-readable storage medium having stored thereon computer-executable instructions that, when executed, configure at least one processor to:

a) acquire planned control point data describing predetermined control points each describing a predetermined operational state of the radiation treatment apparatus, the control points having a predetermined temporal order in which they are planned to be assumed by a radiation treatment apparatus and each control point being associated with a predetermined planned relative position between an anatomical body part of a patient's body and a monitoring imaging apparatus, wherein the planned control point data comprises planned position data describing planned relative positions between the anatomical body part and a treatment beam source of the radiation treatment apparatus and, for each at least one planned relative position, the operational state as a reference dose being a predetermined amount of a planned treatment dose associated with the respective at least one planned relative position, wherein each control point is described by at least one of planned relative positions;

b) determine current control point data describing whether the radiation treatment apparatus has assumed a predetermined control point, wherein the current control point data comprises monitoring dose data describing the current operational state as a monitoring dose being an amount of the planned treatment dose associated with at least one of a monitoring image or the at least one actual relative position between the anatomical body part and the treatment beam source;

c) acquire monitoring image data describing at least one digital medical monitoring image of the anatomical body part in at least one monitoring relative position between the anatomical body part and the monitoring imaging apparatus, wherein the monitoring imaging apparatus is used to generate the monitoring image;

d) acquire patient image data describing a predetermined medical image of the anatomical body part;

e) determine, based on the monitoring dose data and the planned control point data, corresponding reference dose data describing a corresponding reference dose being the reference dose corresponding best within a predetermined interval to the monitoring dose;

f) determine, based on the patient image data and the corresponding reference dose data, comparison image data describing at least one digital medical comparison image of the anatomical body part in the monitoring relative position, wherein the monitoring relative position is the planned relative position between the anatomical body part and the monitoring imaging apparatus; and g) determine, based on the comparison image data and the monitoring image data, position deviation data describing a positional deviation between (i) the planned relative position associated with the planned control point assumed by the radiation treatment apparatus and (ii) the monitoring relative position on the other hand, wherein the computer-executable instructions, when executed, further configure the processor to:

h1) generate the comparison image data if the current control point data describes that the radiation treatment apparatus has assumed a predetermined control point, or h2) generate the monitoring image data if the current control point data describes that the radiation treatment apparatus has assumed a predetermined control point.

19. A system for determining a deviation between a planned and an actual relative position between an anatomical body part and a treatment beam source, the system comprising:

at least one electronic data storage device storing at least planned control point data;
a medical imaging device for generating a monitoring image, the medical imaging device being operably coupled to at least one processor for transmitting a signal to the at least one processor corresponding to monitoring image data; and
a radiation treatment apparatus comprising a treatment beam source,
wherein the at least one processor is operably coupled to the at least one electronic data storage device for acquiring, from the at least one data storage device, at least one of patient image data or the planned control point data, and for issuing a command to the radiation treatment apparatus for controlling the treatment beam source on the basis of position deviation data, wherein the at least one processor is further configured to:

a) acquire the planned control point data describing predetermined control points each describing a predetermined operational state of the radiation treatment apparatus, the control points having a predetermined temporal order in which they are planned to be assumed by the radiation treatment apparatus and each control point being associated with a predetermined planned relative position between an anatomical body part of a patient's body and the medical imaging device, wherein the planned control point data comprises planned position data describing planned relative positions between the anatomical body part and the treatment beam source of the radiation treatment apparatus and, for each at least one planned relative position, the operational state as a reference dose being a predetermined amount of a planned treatment dose associated with the respective at least one planned relative position, wherein each control point is described by at least one of planned relative positions;

b) determine current control point data describing whether the radiation treatment apparatus has assumed a predetermined control point, wherein the current control point data comprises monitoring dose data describing the current operational state as a monitoring dose being an amount of the planned treatment dose associated with at least one of the monitoring image or the at least one actual relative position between the anatomical body part and the treatment beam source;

c) acquire the monitoring image data describing at least one digital medical monitoring image of the anatomical body part in at least one monitoring relative position between the anatomical body part and the medical imaging device;

d) acquire the patient image data describing a predetermined medical image of the anatomical body part;

e) determine, based on the monitoring dose data and the planned control point data, corresponding reference dose data describing a corresponding reference dose being the reference dose corresponding best within a predetermined interval to the monitoring dose;

f) determine, based on the patient image data and the corresponding reference dose data, comparison image data describing at least one digital medical comparison image of the anatomical body part in the monitoring relative position, wherein the monitoring relative position is the planned relative position between the anatomical body part and the medical imaging device; and g) determine, based on the comparison image data and the monitoring image data, the position deviation data describing a positional deviation between (i) the planned relative position associated with the planned control point assumed by the radiation treatment apparatus and (ii) the monitoring relative position on the other hand;

wherein the at least one processor is further configured to:

h1) generate he comparison image data if the current control point data describes that the radiation treatment apparatus has assumed a predetermined control point, or h2) generate the monitoring image data if the current control point data describes that the radiation treatment apparatus has assumed a predetermined control point.

* * * * *

UNITED STATES PATENT AND TRADEMARK OFFICE
CERTIFICATE OF CORRECTION

PATENT NO. : 10,543,381 B2
APPLICATION NO. : 16/438975
DATED : January 28, 2020
INVENTOR(S) : Kajetan Berlinger et al.

Page 1 of 1

It is certified that error appears in the above-identified patent and that said Letters Patent is hereby corrected as shown below:

In the Claims

Column 15, Line 50 of Claim 1, "body park" should be changed to "body part".

Signed and Sealed this
Third Day of March, 2020

Andrei Iancu
*Director of the United States Patent and Trademark Office*